United States Patent [19]

Bonneau et al.

[11] 4,056,614

[45] Nov. 1, 1977

[54] IMMUNITY DEPRESSANT MEDICINE

[76] Inventors: Marc Bonneau, 18, rue de Tourville, 69005 Lyon; Mireille Latour, 23, Les Sabines, 69130 Ecully, both of France

[21] Appl. No.: 636,611

[22] Filed: Dec. 1, 1975

Related U.S. Application Data

[63] Continuation-in-part of Ser. No. 399,496, Sept. 21, 1973, abandoned.

[30] Foreign Application Priority Data

Sept. 22, 1972   France .................................. 72.33703

[51] Int. Cl.² ........................ A61K 35/50; A61K 39/00

[52] U.S. Cl. ..................................... 424/105; 424/85; 424/177; 260/112 B

[58] Field of Search ............... 424/105, 85; 260/112 B

[56] References Cited

PUBLICATIONS

Skvaril et al., Chem. Abst., vol. 63 (1965), p. 8639c.

*Primary Examiner*—Sam Rosen
*Attorney, Agent, or Firm*—Cushman, Darby & Cushman

[57] ABSTRACT

Immunity-depressing biologic medicine comprising in serum an effective amount of immuno-depressive gamma-globulins obtained by elution of ground and washed human placental tissue with an acid buffer and separation from the eluate of the thus-freed gamma-globulins by precipitation.

16 Claims, 1 Drawing Figure

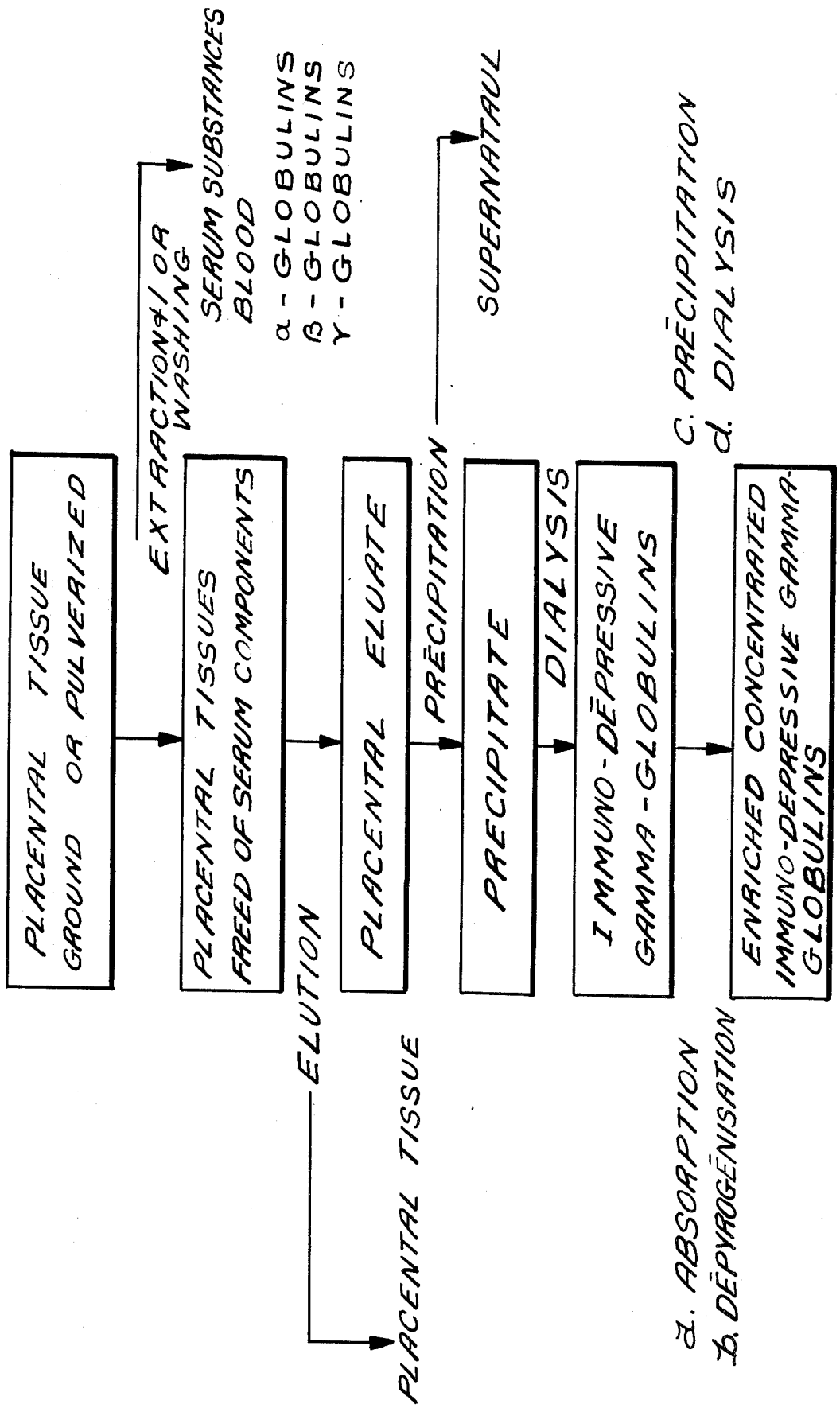

IMMUNITY DEPRESSANT MEDICINE

This is a continuation-in-part application of United States patent application Ser. No. 399,496, filed Sept. 21, 1973, now abandoned, said application Ser. No. 399,496 relied upon and incorporated herein by reference.

The present invention relates to an immunity depressing biologic medicine and to a process for preparing the same.

This invention relates to a process for extracting immuno-depressive gamma-globulins from placental tissue, particularly from human placental tissue, and the products produced thereby.

The immuno-depressive gamma-globulins obtained in accordance with the process provide immuno-depressive medicines which allow for effective depression of the immunological system, mainly by inhibiting organic tissue immunity agents.

The aforementioned type of medicine may be used for treatment to avoid rejection of grafts, as well as for treatment of immunitary illnesses with cellular support in humans. The immuno-depressive gamma-globulins, obtained by the process of the invention are completely different from gamma-globulins obtained by conventional methods of deriving gamma-globulins from blood or from placental serum, the latter commonly being referred to as "placental gamma-globulins" in that "placental gamma-globulins" have practically no immuno-depressing effect.

Placental gamma-globulins are prepared by washing human placental tissue with a saline solution or even by simple extraction of the tissues followed by precipitation of the gamma-globulins in a solvent such as methanol.

The conventional methods do not allow for the extraction of immuno-depressive gamma-globulins because the immuno-depressive gamma-globulins are fixed directly onto the placental tissue by a bond of the "antigen-antibodies" type and are not separated by the usual techniques for extracting "placental gamma-globulins."

Indeed, it has been determined that immuno-depressive gamma-globulins can only be extracted by employing extraction solutions having an acidic pH or a practically neutral pH; when a neutral pH is used, strong ionic solutions must be used.

The process according to the invention for extracting immuno-depressive gamma-globulins from placental tissue is realized by grinding or pulverizing placental tissue. After pulverization of the placental tissue, the placental material is extracted with a saline solution. An example of the grinding apparatus which can be used in the process is U-Turrax TP 45/2 which can be used at a speed of about 10,000 cycles per minute for 15 minutes.

Placental tissues thus pulverized are then subjected to an extraction and/or to several washings; extraction and washing may be undertaken with water or with saline solution. Preferably, the material which has been ground and possibly extracted is washed several times to eliminate all substances, which are not to be isolated, such as, blood, alpha-, beta-, and gamma-globulins, albumin and the like.

The saline solutions, which may be used in accordance with the invention to treat the placental tissue in the step of extracting and/or washings, can be PBS(NaCl:8g-KCl:0.2 grams-$Na_2HPO_4(2H_2O)$: 1.44 grams-$KH_2PO_4$:0.2 grams-distilled water, q.s.p. 1 liter); neutral salt solutions (solutions of sodium chloride or potassium chloride of concentrations ranging between 0.1 M – 2.5 M); solutions of acid salts (sodium or potassium phosphate salts, disodium or dipotassium citrate, of a concentration of 0.1 M); hydrochloric acid solutions at appropriate pH.

The placental tissues which have been washed and freed of serum substances are then subjected to the next principal step associated with the extraction process of the invention which is the step of elution. The elution step as described in our prior application Ser. No. 399,496 (of which this application is a continuation-in-part) may be undertaken at temperatures between 10° and 38° C. Generally this step is undertaken with a buffer solution having a pH of about between 2 and 7.5, at a temperature between 0° to 40° C., preferably between 4° to 10° C., for a period of time ranging between 10 minutes and 1 hour, and preferably between 10 minutes and less than 30 minutes.

The buffer solutions which may be used in accordance with the invention include glycine-hydrochloric acid, acetic acid-sodium acetate, citric acid-sodium citrate, lactic acid-sodium lactate, maleic acid-sodium maleate and succinic acid-sodium borate solutions.

The aforementioned solutions are characterized by a pH of about between 2 and 4 and preferably have a pH between 2 and 3.5.

The elution step of the invention can also be undertaken at a pH of 6.5 to 7.5 by employing a solution of high ionic salt concentration, such as 4 M sodium chloride or 2 M di-sodium or mono-potassium phosphate.

The step of elution can be repeated several times to augment the recovery of the desired product.

The placental eluate is then separated from the placental tissue by conventional methods, such as by centrifugation.

The principal eluate is obtained eventually as a mixture with other secondary eluates and is then subjected to a precipitation step to precipitate the immuno-depressive gamma-globulins.

This precipitation is undertaken in accordance with the conventional techniques, of Cohn, which involves employing as a precipitating agent an alcohol or a mixture of alcohols such as ethanol, methanol, or a mixture of methanol and ethanol.

This step of the precipitation is generally undertaken at about a neutral pH, the pH of the placental eluate being maintained at neutrality, by the addition of sodium hydroxide or a basic buffer Tris HCl of a pH 10 for example.

The precipitation of immuno-depressive gamma-globulins can also be undertaken according to other conventional techniques, including use and addition of polyphosphoric acid or addition of ammonium sulphate to the placental eluate.

The precipitate which is obtained is subjected to several consecutive dialysis against water which ultimately results in isolating the desired immuno-depressive gamma-globulins according to the invention.

In particular, this dialysis permits the elimination of the alcohol used in the precipitation step.

The dialysis is usually undertaken at a temperature of less than 4° C.

The different stages of the process for obtaining the immuno-depressive gamma-globulins are set forth in the flow sheet of the drawing.

According to the following embodiment of the invention, it is possible to obtain immuno-depressive gamma-globulins in an extended purified form.

The immuno-depressive gamma-globulins, isolated after dialysis, can be subjected, at temperatures less than 10° C., and preferably at 4° C., to absorption in the presence of an absorbing agent such as bentonite, aerosil, activated carbon, or synthetic polymers.

The proportion of absorbing agent is generally between 250 grams to 500 grams per kilogram of substance to be purified. After agitating a mixture of the absorbing agent and gamma-globulins for about 15 minutes, and after centrifugation, then neutralization, immuno-depressive gamma-globulins are obtained which are free of polysaccharides and lipoproteins.

Following this operation of eliminating the lipoproteins and polysaccharides, the immuno-depressive gamma-globulins can also be subjected to a step to eliminate the pyrogenic substances. If this step is undertaken, the immuno-depressive gamma-globulins are subjected to chromatography on DEAE-cellulose and treated at a temperature of between 35° to 45° C., for an hour to three hours in the presence of aluminum hydroxide, in proportions of about 100 grams aluminum hydroxide for each 100 grams of the immuno-depressive gamma-globulins to be treated.

The immuno-depressive gamma-globulins are then precipitated according to the described methods, subjected to dialysis against water.

Such a treatment results in greatly enriched immuno-depressive gamma-globulins.

Immuno-electrophoretic analysis of the immuno-depressive gamma-globulins proves that the gamma-globulins are principally of type G rather, than gamma-globulins of type A and M.

The gamma-globulins of the invention react and precipitate with a rabbit or sheep anti-human-IG serum; they exhibit no, or only very weak, cytotoxicity for human lymphocytes in the presence of a complement. If cytotoxic activity is detected, the product can be subjected to an enzymatic degradation by employing pepsin or papain to obtain immuno-globulin fragments $Fab_2$ and $Fab'_2$, which are not cytotoxic and immuno-depressive.

The present invention also relates to immuno-depressive gamma-globulins derived from the process described above.

The immuno-depressive gamma-globulins, produced in accordance with the aforementioned process, have the following characteristics:

They react and precipitate with a rabbit or sheep anti-human-Ig serum; they exhibit no, or only a very weak, cytotoxicity for human lymphocytes in the presence of a complement. On the other hand, these immuno-depressive gamma-globulins exhibit inhibiting properties of immuno-cyto-adherence, which can be verified by means of the rosette test, which consists in observing the formation of rosettes, that is, the agglutination of sheep red blood cells around human lymphocytes in the presence of a guinea pig complement.

The present invention also relates to a process for producing a medicine, and the medicine produced thereby, which comprises washing powdered or ground placental tissue, extracting from said tissue, the gamma-globulins fixed thereon, separating the thus-extracted or freed gamma-globulins from the tissular elements and providing the resulting immuno-depressive gamma-globulins in additional dosage form. The immuno-depressive gamma-globulins are admixed with a suitable pharmaceutical carrier to produce a medicine in dosage form.

Preferably, the pharmaceutical vehicle is physiological water.

The immuno-depressive activity of the immuno-depressive gamma-globulins in accordance with the invention can be established by different tests.

The gamma-globulins according to the invention inhibit a mixed lymphoycytary reaction, that is to say, the transformation of human lymphocytes in a culture proves the existence of two histo-incompatible organisms. The mixed lymphocytary reaction is considered as equivalent in vitro, of the cellular reaction induced by the introduction of a graft incompatible with an organism.

The inhibitor standard of the immuno-depressive gamma-globulins preparation on lymphoblastic transformation can be measured in a culture medium, by the mixture of lymphocytes coming from two organisms with different donors.

This measurement is undertaken by a liquid scintillation count of the radioactivity incorporated into the new cells in culture after exposing for 16 hours in the presence of 1 μc (microcurie) of $3_1$ H methyl thymidine[specific activity of 100 μc/mM (micromole)]. The 50% inhibiting standard is about 1/100 for the preparation disclosed in the Example (or 0.05 mg/ml).

The immuno-depressive gamma-globulins according to the invention also inhibit the transformation and proliferation of human lymphocytes cultivated in the presence of antigens, such as tuberculin, and various other antigens.

The gamma-globulins, in accordance with the invention also inhibit, in concentrations higher than in the preceding tests, the transformation and proliferation of human lymphocytes induced by mitogenes such as phytohemagglutinin.

Medicines produced in accordance with the invention are particularly adapted to the preventive treatment of the rejection of grafts in human beings, as well as for treatment of self-immune diseases.

In accordance with an alternative embodiment of the invention, the medicine can be combined with other immuno-depressive agents, such as antilymphocyte serum, prepared by immunization of an animal with lymphocytes of human origin or monkey origin, or immuno-depressive chemical agents.

According to the invention, the dose of immuno-depressive gamma-globulins, to be administered to adult human beings can be, for example, from of about 50 mg to 500 mg. per day, for a period of several days.

Obviously, the exact dose depends upon the ailment or condition to be treated, as well as upon the concomitant immuno-depressive drug therapy, such as antilymphocytary serum or chemical immuno-depressive.

The medicine in accordance with the invention can be utilized for intra-arterial perfusion of transplanted organs, at the time of the graft and it can be administered parentally post-operatively.

The following examples illustrate preparation of immuno-depressive gamma-globulins according to the invention.

EXAMPLE I

A mixture of 30 fresh non-frozen human placentas, preserved at +4° C in a PBS buffer (NaCl — 8g; KCl — 0.2g; $Na_2HPO_4(2H_2O)$ —1.44g; $KH_2PO_4$ — 0.2g and distilled water q.s.p. 1 liter) is ground or pulverized yielding on separation 8.8 kilos of tissue and 6 liters of placental blood. Grinding and pulverization were undertaken in a U-Turrax TP 45/2, at a rate of 10,000 cycles/mn. for 15 minutes. A PBS buffer wash is then carried out at a rate of 4 liters of buffer per kilogram of placental tissue, so that the weight of the tissue matter is adjusted to 7.8 kilograms after washing.

Five consecutive washings are thus performed. In the last washing, the washing liquid contains practically no serous substance and no protein. After the last washing, the tissue matter weight is reduced to 5 kilograms.

A first extraction or elution is then carried out at a pH of 2.2 using a mixture of 5 kilograms of washed tissue and 20 liters of glycine-HCl buffer with moderate agitation for a period of about 30 minutes at 37° C. One liter of glycine-HCl buffer employed is prepared by admixing the following two solutions in the following proportions: 420 ml of a solution of HCl (0.1M) diluted to 1120 ml and 580 ml of a saline solution of glycocoll - 4.3g; NaCl - 3.39g and distilled water q.s.p. 580 ml.

The resulting extract is then centrifuged yielding 20 liters of supernatant and 4.8 kilos of tissue material. In order to augment the amount of final product, the tissue material, a second, third and fourth extraction or elution in a manner exactly as that in the presence of a glycine-HCl buffer.

The pH of this supernatant is adjusted to about 7 by the addition thereto of a Tris-HCl buffer (pH 10). One liter of this solution contains tris-hydroxymethylaminomethane 0.1 M (12.1 g); distilled water q.s.p. 1 liter and HCl q.s.p. pH 10.

The precipitate which forms is then eliminated, and a solution of about 29 liters is obtained to which ethanol is added until a concentration of 40% is achieved, thus yielding 210 grams of precipitate which arre collected and dialysed first with water, and then with said PBS buffer. A second dialysis with water is then carried out, finally yielding 0.200 l containing said immuno-depressive gamma-globulin at a concentration of 7.32 grams per liter.

That amount of recovered product of the invention is a result of precipitation of first eluate. If as set forth above, a second extraction of tissue material, followed by precipitation, is undertaken, combination of the first and second eluates would result in increasing the yield of immuno-depressive gamma-globulins by about 10%.

EXAMPLE II 1,200 kg of frozen human placentas are subjected to grinding with the aid of conventional grinder, after extraction which eliminates the major part of the serum substance, including blood, alpha-globulins, beta-globulins, and gamma-globulins; after this step 600 kg of placental tissue is recovered. The placental tissue obtained in this manner is then subjected to a step of washing a sodium acid phosphate saline solution at neutral pH, the solution having a concentration of 0.1 M at a temperature of about 20° C. The wash is repeated three or four times with about 400 liters of solution for each 100 kg of placental tissue. This step of washing is optional to permit purification of placental tissue before the step of elution.

The placental tissues which are purified in this manner are then subjected to an elution step, using a buffer solution of citric acid-citrate at a pH 3 for a fifteen minute period at 10° C., using 400 liters of solution for 100 kg of placental tissue.

The placental eluate is then recovered by centrifugation, filtration or extraction according to conventional techniques.

The recovered placental tissues can again be subjected to several elutions under the same conditions as above to improve the amount of recovery of the final product. (See Example I above).

The pH of the placental eluate is then adjusted to a pH of 7 by the addition of sodium hydroxide.

Eventually, a precipitate will form which is isolated by centrifugation, filtration or extraction.

The placental eluate is then subjected to the step of precipitation by addition of a 50:50 methanol-ethanol mixture in order to dilute the concentration to a final concentration of 30% alcohol.

The precipitate obtained is then subjected to dialysis, against water to eliminate the alcohol and then is subjected to a dialysis against a PBS buffer, followed by another dialysis against water.

The immuno-depressive gamma-globulins obtained in this manner can be utilized, as recovered, in the preparation of medicines according to the invention or can be subsequently subjected to a series of stages of purification according to the following conditions:

The immuno-depressive gamma-globulins obtained after dialysis against water are subjected to an absorption step in the presence of bentonite and aerosil at a temperature of 4° C. The quantity of bentonite used is about 15 grams per each kg of solution and the quantity of aerosil is about 2.5 grams per each kg of solution. After agitating, for 15 minutes and then centrifugation, followed by neutralization, immuno-depressive gamma-globulins, freed of tissular polysaccharides and lipoproteins are recovered; then they are purified by ion exchange chromatography on batch of Q A E Sephadex.

The immuno-depressive gamma-globulins are then subjected to a step of depyrogenization in the presence of aluminum hydroxide in amounts of about 100 grams of aluminum hydroxide for each and every 100 grams of immuno-depressive gamma-globulins at a temperature of 35° to 45° for about an hour-and-a-half.

The immuno-depressive gamma-globulins are then precipitated with ethyl alcohol in a manner such that the final concentration is in the order of about 40%.

After dialysis against water, then against a PBS buffer, and a final dialysis against water, a final product of 60 grams of enriched (concentrated) immuno-depressive gamma-globulins is obtained.

What is claimed is:

1. A process for extracting immuno-depressive gamma-globulins from human placental tissue which has been ground or powdered comprising the following steps:
    a. Washing the ground placental tissue to remove serous substances therefrom;
    b. Eluting the placental tissues, freed of serous substances, with a buffer solution to form an eluate; and freeing the eluate of any tissue material and precipitates wherein the elution of the placental tissue is undertaken at a pH of about between 2 and 3.5 with said buffer solution and at a temperature ranging between about 10° to 38° C;
    c. Adding ethanol to said eluate to precipitate the immuno-depressive gamma-globulins; and
    d. Dialyzing the immuno-depressive gamma-globulins with water.

2. Process according to claim 1 wherein step b is carried out for a period of about 30 minutes.

3. Process according to claim 1 wherein the extraction is carried out at a temperature of about 37° C.

4. Process according to claim 1 wherein in step b the gamma-globulins are separated from the tissue elements by centrifugation and are present in the resulting eluate.

5. Process according to claim 1 wherein the pH of the supernatant is adjusted to essentially a neutral value, ethanol is added and that at least one dialysis is performed to concentrate said gamma-globulins.

6. Process according to claim 1 wherein said placental tissue is washed with a PBS buffer.

7. Process according to claim 5 including several successive washings.

8. Medicine comprising gamma-globulins produced by the process of claim 1 wherein said gamma-globulins are characterized in that they
   a. react with an animal anti-human-Ig serum
   b. have almost no lymphocytotoxicity;
   c. inhibit the lymphoblastic transformation of human lymphocytes stimulated by phytohemagglutinin and by various antigens; and
   d. inhibit the lymphoblastic transformation of histo-incompatible human lymphocytes in mixed culture.

9. Medicine according to claim 8 wherein said gamma-globulins are contained in a therapeutic serum for use by man.

10. Medicine according to claim 9 in the form of a dosage for humans containing about 500 mg of proteins.

11. Medicine according to claim 10 which also includes at least one other immuno-depressant agent.

12. Medicine according to claim 11 wherein said other immuno-depressant agent is human anti-lymphocyte serum.

13. The process of treating graft rejection in human beings suffering from auto-immunity comprising administrating the medicine of claim 8 in an amount of the order of 500 mg per day.

14. A process for extracting immuno-depressive gamma-globulins from human placental tissue which has been ground or powdered comprising the steps of:
   a. Washing the ground placental tissue to remove serous substances therefrom;
   b. Eluting the placental tissues, freed of serous substances, with a buffer solution having an acid pH of 6.5 to a basic pH of 7.5 to form an eluate; and freeing the eluate of any tissue material and precipitate;
   c. Adding ethanol to said eluate to precipitate the immuno-depressive gamma-globulins; and
   d. Dialyzing the immuno-depressive gamma-globulins with water.

15. A process for extracting immuno-depressive gamma-globulins from human placental tissue which has been ground or powdered comprising the following steps:
   a. Washing the ground placental tissue to remove serous substances therefrom;
   b. Eluting the placental tissues, freed of serous substances, with a buffer solution to form an eluate; and freeing the eluate of any tissue material and precipitates wherein the elution of the placental tissue is undertaken with said buffer solution having an acid pH and at a temperature ranging between about 10° to 38° C;
   c. Adding ethanol to said eluate to precipitate the immuno-depressive gamma-globulins; and
   d. Dialyzing the immuno-depressive gamma-globulins with water.

16. A process for extracting immuno-depressive gamma-globulins from human placental tissue which has been ground or powdered comprising the following steps:
   a. Washing the ground placental tissue to remove serous substances therefrom;
   b. Eluting the placental tissues, freed of serous substances, with a buffer solution to form an eluate; and freeing the eluate of any tissue material and precipitates wherein the elution of the placental tissue is undertaken with said buffer solution which has a substantially neutral pH and at a temperature ranging between about 10° to 38° C;
   c. Adding ethanol to said eluate to precipitate the immuno-depressive gamma-globulins; and
   d. Dialyzing the immuno-depressive gamma-globulins with water.

* * * * *